United States Patent
Gaylord et al.

(10) Patent No.: US 7,651,472 B2
(45) Date of Patent: Jan. 26, 2010

(54) ANKLE STABILIZING APPARATUS HAVING A PIVOTABLE STIFFENING UNIT

(75) Inventors: Robert Scott Gaylord, Matthews, NC (US); Eric Lee Gaylord, Matthews, NC (US)

(73) Assignee: Medical Specialties, Inc., Charlotte, NC (US)

(*) Notice: Subject to any disclaimer, the term of this patent is extended or adjusted under 35 U.S.C. 154(b) by 686 days.

(21) Appl. No.: 11/370,577

(22) Filed: Mar. 8, 2006

(65) Prior Publication Data

US 2007/0213649 A1    Sep. 13, 2007

(51) Int. Cl.
*A61F 5/00* (2006.01)
*A61F 13/00* (2006.01)

(52) U.S. Cl. .............. 602/27; 602/5; 602/23; 602/60; 602/65

(58) Field of Classification Search ............. 602/27–29, 602/60–62, 65, 5, 23, 66; 128/882; D24/192, D24/191
See application file for complete search history.

(56) References Cited

U.S. PATENT DOCUMENTS

| | | | |
|---|---|---|---|
| 4,651,726 A | 3/1987 | Holland | |
| 4,771,768 A * | 9/1988 | Crispin | 602/16 |
| 4,878,504 A * | 11/1989 | Nelson | 602/27 |
| 5,067,486 A | 11/1991 | Hely | |
| 5,069,202 A | 12/1991 | Prock | |
| 5,209,722 A | 5/1993 | Miklaus et al. | |
| 5,242,379 A | 9/1993 | Harris et al. | |
| 5,678,330 A * | 10/1997 | Van Dyke et al. | 36/89 |
| 5,778,563 A | 7/1998 | Ahlbäumer | |
| 5,795,316 A | 8/1998 | Gaylord | |
| 6,021,780 A | 2/2000 | Darby | |
| 6,053,884 A | 4/2000 | Peters | |
| 6,379,321 B2 | 4/2002 | Gaylord et al. | |
| 6,629,945 B1 | 10/2003 | Stromgren | |
| 2003/0083603 A1 | 5/2003 | Nelson | |
| 2004/0215123 A1 | 10/2004 | Slautterback et al. | |
| 2006/0084899 A1 * | 4/2006 | Verkade et al. | 602/27 |

* cited by examiner

*Primary Examiner*—Kim M Lewis
(74) *Attorney, Agent, or Firm*—Summa, Additon & Ashe, P.A.

(57) ABSTRACT

An apparatus for stabilizing movement of an ankle comprises in one embodiment a flexible body member for receiving a foot and a stiffening unit secured to selected portions of the body member such that the stiffening unit minimizes movement of upper portions of the body member with respect to lower portions of the body member, without obstructing forward and rearward movement of the upper portions of the body member with respect to the lower portions of the body member.

48 Claims, 3 Drawing Sheets

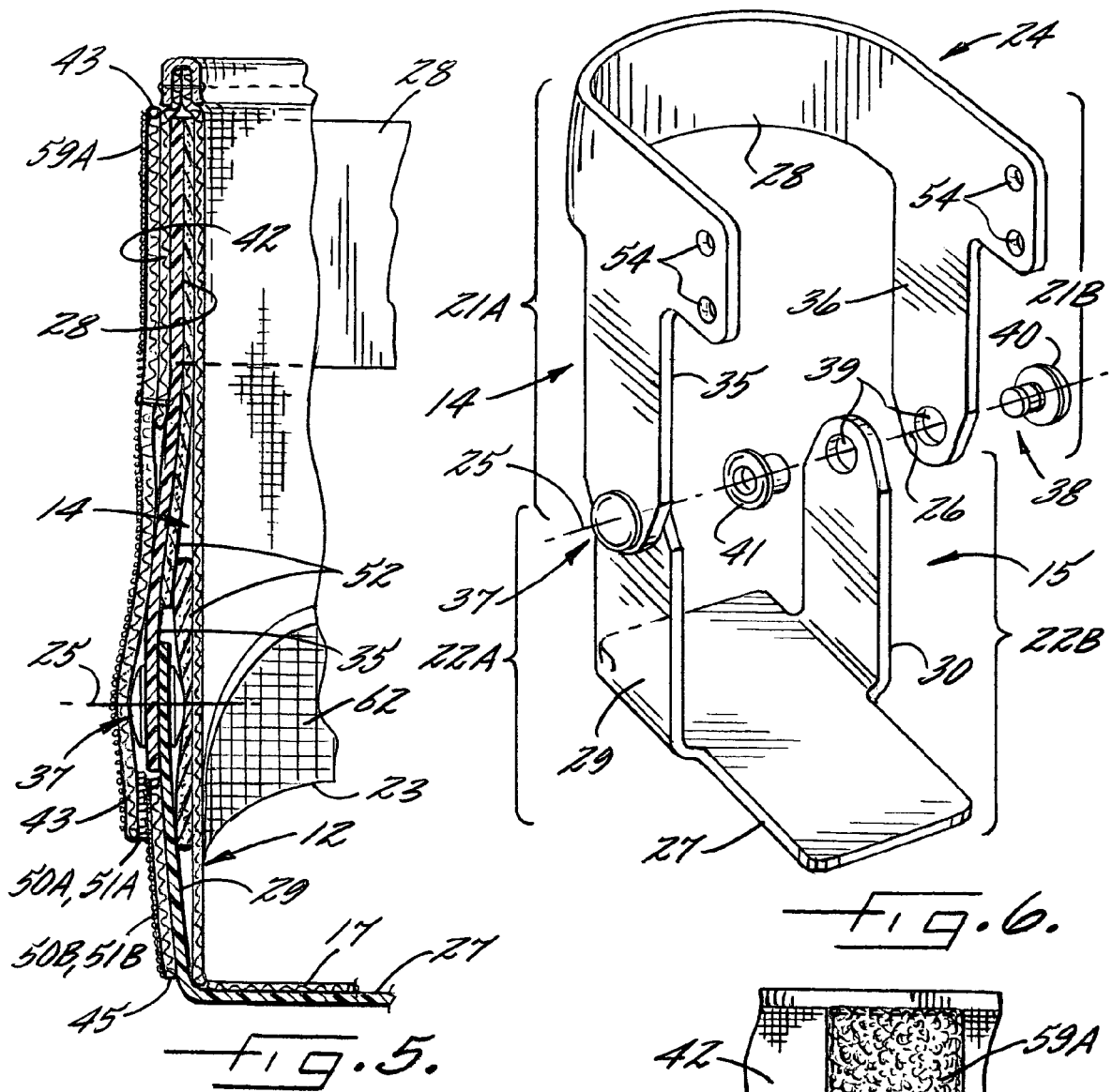
fig.5.
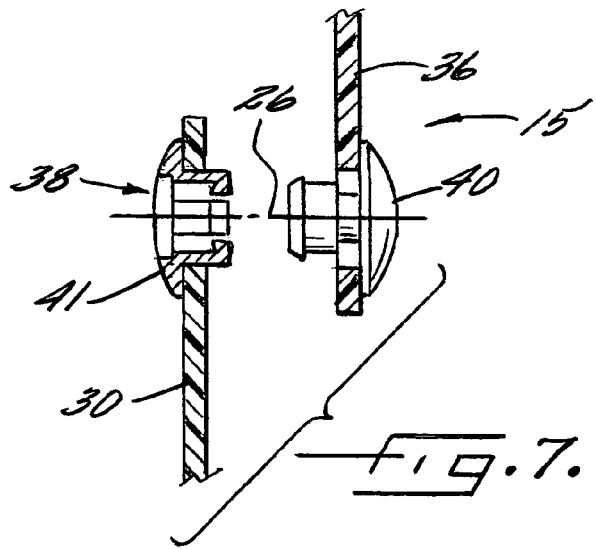
fig.6.
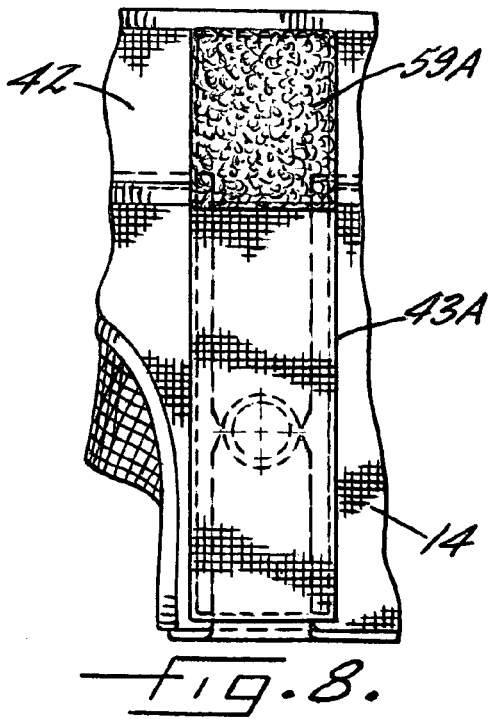
fig.7.
fig.8.

ANKLE STABILIZING APPARATUS HAVING A PIVOTABLE STIFFENING UNIT

FIELD OF THE INVENTION

The invention relates to an ankle stabilizing apparatus for minimizing inversion and eversion of a foot, and more specifically, to a flexible body member and a pivotable stiffening unit secured to selected portions of the body member, wherein the stiffening unit minimizes movement of upper portions of the body member with respect to lower portions of the body member, without obstructing forward and rearward movement of the upper portions of the body member with respect to the lower portions of the body member.

BACKGROUND OF THE INVENTION

As known to participants in athletics, the ankle is often injured as a result of contact with other participants or items of equipment, or as a result of the ankle assuming an unnatural position during play. Injuries typically occur during motions typically associated with athletics such as running, jumping, falling, or the like. Specifically, ankles are particularly vulnerable to sprains, fractures, and the like.

Athletes at risk for ankle injuries often utilize some form of ankle support during participation in sporting events. A large number of ankle injuries occur when the foot rolls inwardly (referred to as "eversion") or outwardly (referred to as "inversion") from the leg. Many athletes rely upon taping to provide supplemental ankle support, whereby the athlete or trainer winds athletic tape around the athlete's ankle to thereby limit the motion of the ankle relative to the leg. Although taping stabilizes the ankle against undesired motion, a number of drawbacks exist. For example, taping may restrict all motion of the ankle, both desirable and undesirable, because the tape is wound circumferentially around the ankle. The restrictive characteristics of taping thus hinder the athlete's ability to perform. Further, tape tends to stretch and loosen as the athlete moves, thereby decreasing its effectiveness in supporting the ankle.

Known stabilizing devices include boot-shaped members or sleeves which cover the athlete's foot and ankle and include supplemental straps designed to wrap around and stabilize certain areas of the individual's foot and ankle. Two such devices are described in commonly-assigned U.S. Pat. Nos. 5,067,486 and 5,795,316, the disclosures of which are incorporated herein by reference.

The majority of ankle sprains are caused by eversion and inversion of the foot. Seventy-five to ninety percent (75-90%) of sprains are attributable to inversion (i.e., outward rolling of the foot). The devices described in the '486 and '316 patents tend to reduce the incidence of injuries resulting from inversion and eversion. Nevertheless, undesirable movement of the ankle may occur as a result of lateral-as well as vertical-movement of upper portions of the body member relative to lower portions of the body member. Thus, a need exists for an ankle stabilizing device which effectively minimizes lateral and vertical movement of the upper portions of the body member relative to the lower portions of the body member. Stated differently, a need exists for an ankle stabilizing device that further minimizes injuries resulting from inversion and eversion of the ankle.

Further, known devices tend to prohibit the forward movement of upper portions of ankle with respect to the foot (i.e., dorsiflexion) and rearward movement of upper portions of ankle with respect to the foot (i.e., flexion). Thus, a need exists for an ankle stabilizing device that provides sufficient support without unduly restricting forward and rearward movement of upper portions of the ankle with respect to the foot.

Known stabilizing devices also include stiffening units or shells which support portions of the athlete's ankle. One such brace is described in U.S. Pat. No. 6,053,884 to Peters and assigned to Athlete Protection Gear, LLC. The '884 patent discloses an ankle brace having a cuff pivotably connected to a base, wherein the cuff is secured to an ankle with a single strap. The cuff includes a left leg and a right leg that are pivotably connected at a rear pivot point. Unfortunately, the brace fails to provide sufficient support for athletes participating in strenuous activities (e.g., basketball and football). Specifically, the pivoting rear section permits lateral movement of the left and right legs, thus failing to prevent inversion and eversion of the ankle during strenuous exercise. Moreover, the pivoting rear section permits the structural separation of the left and right legs of the brace during strenuous exercise such that the single strap securing the brace to the ankle will release. Furthermore, the '886 patent fails to provide sufficient support about portions of the upper ankle. In other words, the cuff structure of the '886 patent does not extend sufficiently about portions of the upper ankle to provide the support necessary to minimize injury.

Another known device is described in U.S. Pat. No. 5,069,202 to Prock that discloses an ankle brace having a foot support shell, an anterior band, lateral and medial uprights that depend from the anterior band and that are pivotably connected to the shell, and straps for securing the brace to the foot. The structural configuration of the foot support shell prohibitively limits the natural movement of the foot during walking and running. Stated differently, the forward and rearward movement of the upper ankle with respect to the foot (i.e., dorsiflexion and flexion) is restricted because the foot support shell encapsulates the entire heel and extends almost the entire length of the bottom of the foot. Further, the three straps disclosed necessarily secure the brace to the foot at fixed points and fail to provide support about the entire ankle.

Unfortunately, the known stiffening units described above are single unit pieces that are not capable of being readily incorporated into a flexible boot shaped body member in a secure fashion that will provide sufficient support for the individual. Thus, still a further need exists for ankle stabilizing apparatus that can be readily incorporated into existing body members in a secure fashion.

OBJECT AND SUMMARY OF THE INVENTION

It is therefore an object of the present invention to provide an ankle stabilizing apparatus which effectively minimizes the occurrence of ankle sprains without unduly restricting the desirable motions of the ankle during athletic activities.

It is also an object of the invention to provide an ankle stabilizing apparatus which effectively minimizes lateral movement of the upper portions of the ankle relative to the lower portions of the foot.

It is a further object of the present invention to provide an ankle stabilizing apparatus that provides sufficient support without unduly restricting forward and rearward movement of upper portions of ankle with respect to the foot.

It is still a further object of the invention to provide an ankle stabilizing apparatus that can be readily incorporated into existing body members in a secure fashion.

The invention meets these objectives with an ankle stabilizing apparatus capable of minimizing lateral movement of upper portions of the body member and ankle with respect to lower sections of the body member and foot, without obstructing forward and rearward movement of upper portions of the body member and ankle with respect to the lower sections of the body member and ankle. In particular, the invention is an ankle stabilizing apparatus having a flexible body member and a stiffening unit secured to selected portions of the body member, wherein the stiffening unit includes a base and a cuff that are pivotably connected.

The foregoing and other objects and advantages of the invention and the manner in which the same are accomplished will become clearer based on the following detailed description taken in conjunction with the accompanying drawings in which:

BRIEF DESCRIPTION OF THE DRAWINGS

FIG. 5 is an enlarged partial front view of the apparatus taken along lines 5-5 of FIG. 3.

FIG. 6 is a perspective view of the stiffening unit of the apparatus.

FIG. 7 is an enlarged and exploded partial front view of a pivotable connection of the apparatus.

FIG. 8 is a perspective view of an alternative embodiment of the apparatus.

DETAILED DESCRIPTION OF THE INVENTION

The present invention will now be described more fully hereinafter with reference to the accompanying drawings, in which a preferred embodiment of the invention is shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 2:
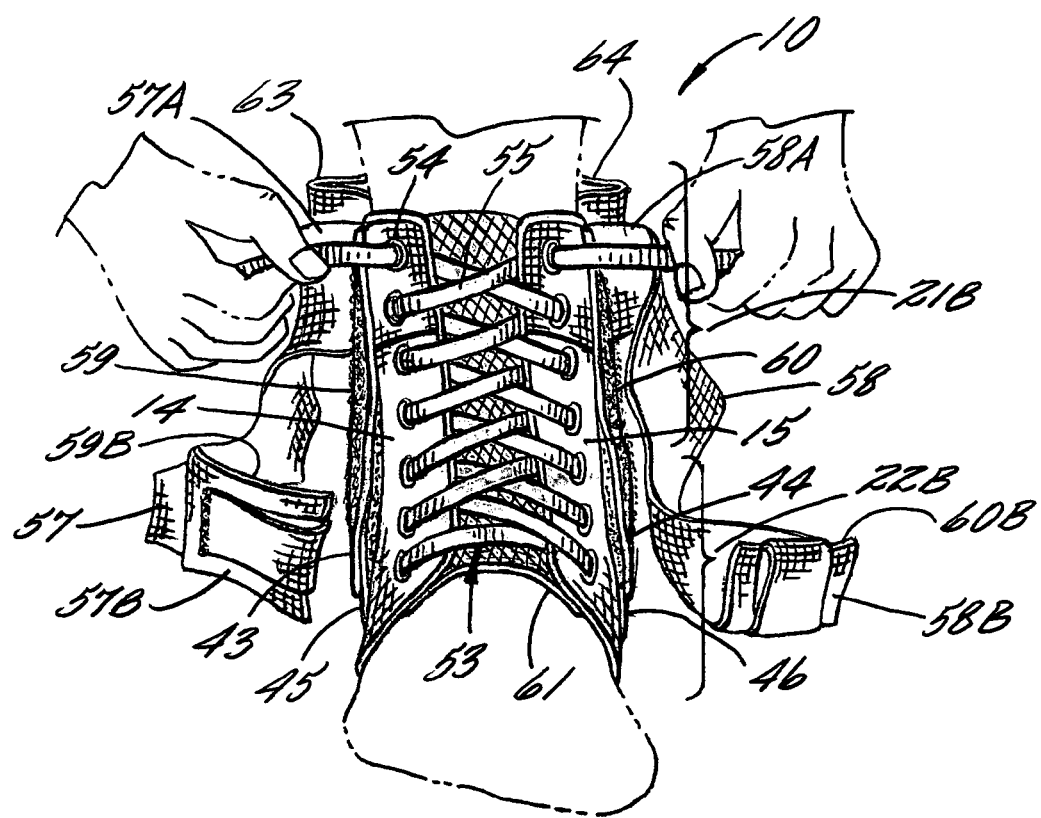
FIG. 2 is a front elevation view of the apparatus as applied to the ankle.

The ankle stabilizing apparatus of the present invention is generally indicated at 10. As illustrated, the apparatus 10 may be worn without an athletic sock such that interior surfaces of the apparatus contact skin of the wearer. Alternatively, the apparatus 10 may be worn over an athletic sock such that interior surfaces of the apparatus contact the sock (not shown). The apparatus 10 is configured for wear on the right or left foot. Therefore FIG. 2 illustrates the apparatus 10 as it appears when worn on a right foot. When worn on a left foot, the apparatus 10 would be a mirror-image version of the one illustrated in FIG. 2, as will be understood by those having ordinary skill in the art.

As used herein, the term "section" is used in conjunction with the ankle stabilizing apparatus 10 of the present invention and refers to the major portions of the body member 11 (e.g., side section and bottom section). It will be understood, however, that a section does not necessarily imply a portion of the body member 11 that is separate from the other portions of the body member. Stated differently, it will be understood that a section may be a separate or integral portion of the body member 11. For example, one embodiment of the body member 11 may be formed from a single piece of material. Thus, a section may refer to a portion of the body member 11 that is defined by a part of the single piece of material forming the body member. That said, it will also be understood that the body member 11 may be formed from multiple pieces of material that are secured to one another to form the body member. In this case, a section may be a separate piece of material forming the body member 11. Those skilled in the art will also appreciate that sections include edges defined as the line of intersection of two surfaces or a border. A "free edge" of a section refers to an edge that does not intersect with another surface or section.

Further, it will also be understood by those of skill in the art that as used herein, the concept of an element (e.g., padding) being "between" two other elements does not necessarily imply that the three elements are contiguous (i.e., in intimate contact). Rather, as used herein, the concept of one element being between two other elements is meant to describe the relative positions of the elements within the apparatus 10 structure, respectively. Similarly, the concept of a first element or section being connected to a second element or section by a third element, "opposite" the second element, merely describes the relative positions of the first and second elements within the apparatus 10 structure.

It will also be understood that the terms "substantially rectangular" and "substantially circular" is meant to succinctly describe a simple geometric shape approximating a rectangle or a circle, respectively. Similarly, the term "substantially parallel" is meant to describe the spatial relationship between, for example, one section or element to another section or element, wherein the relationship is approximately parallel.

Those skilled in the art will also appreciate that the term "substantially adjacent" refers to two or more elements (e.g., sections) that have a common border or are in close proximity to one another. Nevertheless, it will be understood that adjacent may or may not imply contact, but always implies the absence of anything of the same kind in between.

It will also be appreciated that the term "secured" may include sewn, made integral with, adhered with adhesive, or bonded with heat.

Figure 1:
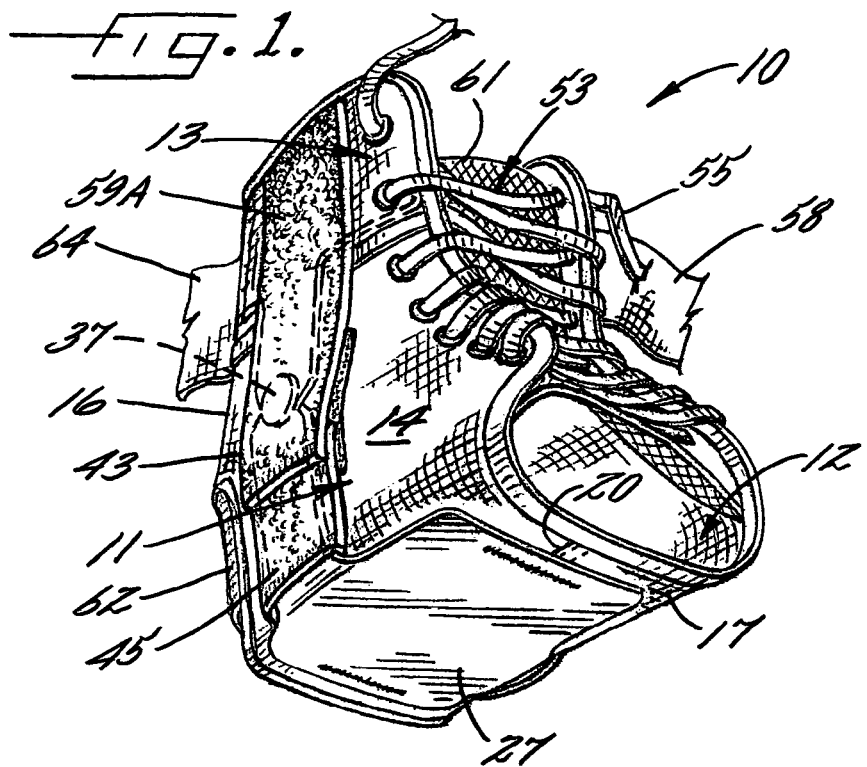
FIG. 1 is a perspective view of an apparatus for stabilizing movement of an ankle.

Referring to FIG. 1, it will be understood that the term "portion" refers to various areas of the apparatus 10. It will be further understood by those skilled in the art that the terms "upper portion" and "lower portion" may also refer to "lower portion" and "upper portion", respectively, dependent upon the perspective of the individual viewing the apparatus. It will also be appreciated that the term "upper" implies the opposite of "lower."

As used herein, it will be understood that the term "elastic" refers to material that is capable of being easily stretched or expanded and resuming its former shape. Stated differently, the term elastic implies the property of resisting deformation by stretching. In a related aspect, it will be understood by those skilled in the art that the term "inelastic" refers to material that resists stretching and elongation.

With reference to the orientation of the brace in FIG. 5, it will be understood by those of skill in the art that the terms "interior surface" and "exterior surface" may be referred to as "inside surface" and "outside surface." Stated differently, as used herein the term interior surface implies the side of the apparatus closest to the ankle or foot of the wearer. Thus, it will be understood that the term exterior surface implies the side of the apparatus opposite the interior surface (i.e., the side farthest from the ankle or foot of the wearer).

Figure 3:
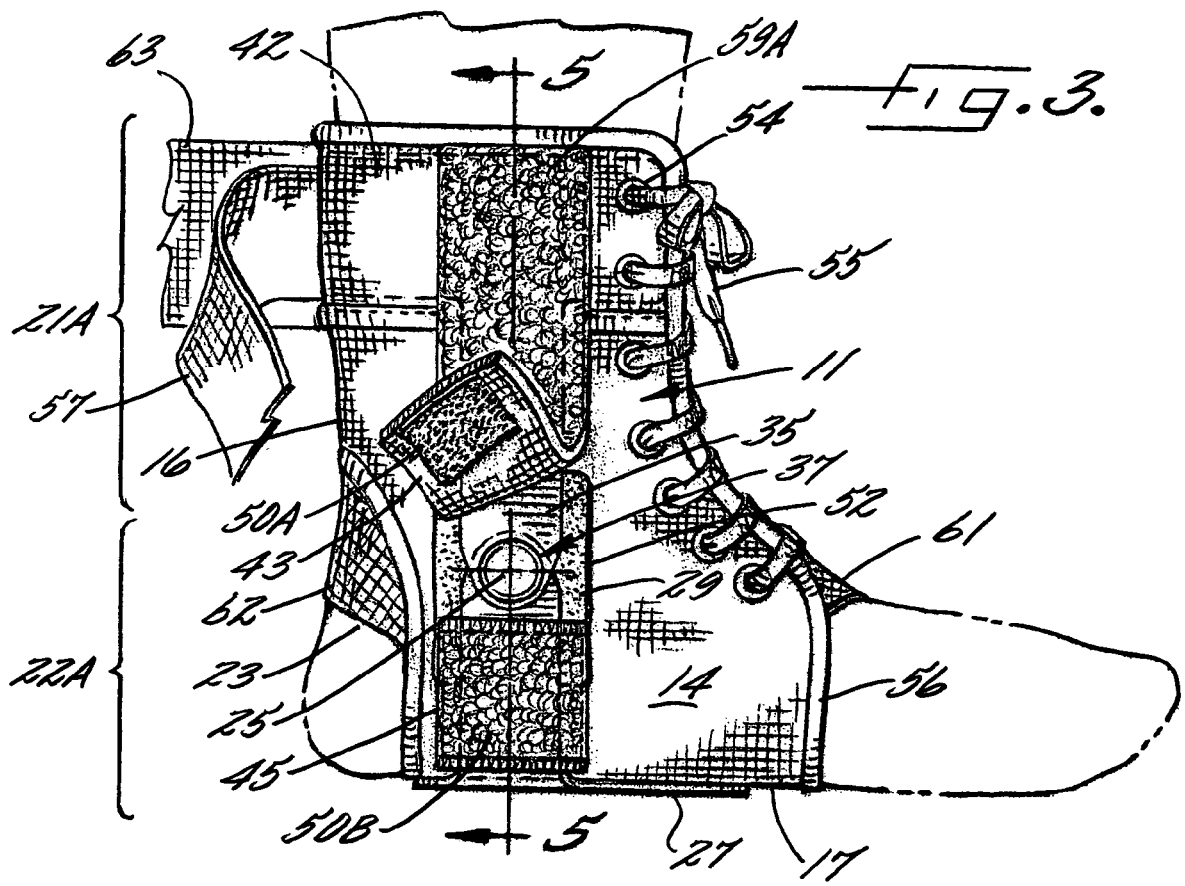
FIG. 3 is a side elevation view of the apparatus as applied to the ankle.

An overall view of a preferred embodiment of an apparatus 10 for stabilizing movement of an ankle which incorporates features of the present invention is set forth in FIG. 3. The apparatus 10 includes a flexible body member 11 which is preferably fabricated from a pliable fabric material. Advantageously, the pliable fabric material will conform to an ankle, yet minimize any stretching familiar to elastic material. As illustrated in FIG. 5, the body member 11 includes an interior surface 12 and exterior surface 13. For ease of reference, the interior and exterior surfaces 12, 13 of the body member 11 will also refer to the interior and exterior surfaces of first and second side sections 14, 15. Thus, the interior surface 12 of the body member 11 may also refer to the interior surface of the first or second side sections 14, 15, and the exterior surface 13 of the body member may likewise refer to the exterior surface of the first or second side sections. It will be understood that the interior surface 12 of the body member 11 is intended for placement adjacent the ankle and the exterior surface 13 is intended for placement facing away from the ankle.

One embodiment of the invention provides a body member 11 fabricated from substantially inelastic fabric material. In this particular embodiment of the invention, the substantially inelastic material is a woven ballistic nylon fabric, as such fabrics have been found to be light weight, while providing a high degree of strength and durability. In addition, such fabrics are generally thin, a particularly desirable characteristic when an individual utilizes the device inside a shoe (not shown).

The sheet of material forming the body member 11 may be formed from one or more sheets of fabric material. In one embodiment, the body member 11 is formed from one sheet of material that is capable of forming a boot-like shape. In this embodiment, the body member is referred to as a "one-piece" body member. The sheet of material is desirably folded and seamed to form a substantially L-shaped configuration for covering at least a lower and rear portion of the individual's foot and ankle. In one embodiment of the body member 11, a single sheet of fabric material is secured (e.g., stitched) at a bottom section 17 of the body member 11 (i.e., under the arch of the foot). In another embodiment of the body member 11, the single sheet is secured at a rear section 16 of the body member (i.e., along the Achilles tendon area of the lower leg). In yet another embodiment, the body member 11 is formed from two sheets of fabric material (i.e., a "multi-piece" body member) wherein the two sheets are secured at the bottom section 17 and rear section 16 of the body member. In yet another embodiment, the body member 11 may be formed from a plurality of sheets secured at one or more sections of the body member.

In one embodiment as depicted in FIGS. 1 and 3, the body member 11 defines a first side section 14, a second side section 15, a rear section 16, and a bottom section 17. The first and second side sections 14, 15 are connected to one another to form the body member 11. In one embodiment, the second side section 15 is connected to the first side section 14 along the bottom section 17 of the body member 11 at a seam 20. The seam 20 may be stitched or connected in any reasonable fashion known to those skilled in the art. Stated differently, the seam 20 extends along the bottom part of the individual's foot (i.e., under the arch of the foot). In another embodiment, the second side section 15 is connected to the first side section 14 along the rear section 16 of the body member 11. In other words, the seam 20 may extend along the Achilles tendon region of the individual's foot.

As illustrated in FIG. 3, upper portions 21A, 21B of the first and second side sections 14, 15 define the rear section 16 of the body member 11. The rear section 16 of the body member 11 provides spacing between the upper portions 21A, 21B of the first and second side sections 14, 15. The bottom section 17 of the body member 11 is defined by lower portions 22A, 22B of the first and second side sections 14, 15, respectively, as illustrated in FIG. 1. In similar fashion, the bottom section 17 of the body member 11 provides spacing between the lower portions 22A, 22B of the first and second side sections 14, 15. As applied to the ankle, the body member 11 further defines at least one opening 23 for receiving the heel of an individual as illustrated in FIG. 3.

Figure 4:
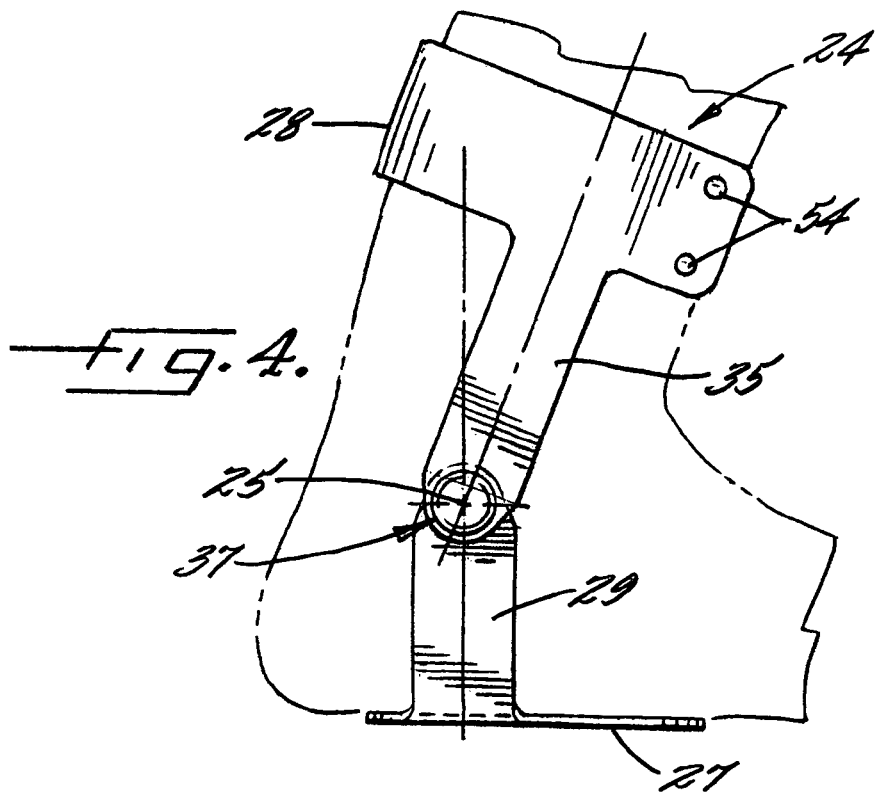
FIG. 4 is a side elevation view of the stiffening unit of the apparatus as applied to the ankle.

Referring to FIGS. 4 and 6, the invention further provides a stiffening unit 24 that is secured to selected exterior portions of the body member 11 (see FIGS. 1 and 3). The stiffening unit 24 includes pivot points 25, 26 positioned between an upper end and a lower end of the stiffening unit. In one embodiment the stiffening unit 24 is formed from polymeric material. Nevertheless, it will be understood that the stiffening unit 24 may be formed from any type of commercially available material that is semi-rigid and capable of being shaped. Advantageously, the stiffening unit 24 minimizes lateral movement of upper portions 21A, 21B of the first and second side sections 14, 15 of the body member 11 with respect to the bottom section 17. Moreover, the stiffening unit 24 minimizes compression (or vertical movement) of the upper portions 21A, 21B of the body member 11 with respect to the bottom section 17 because the stiffening unit is secured to upper and lower portions of the body member. For example, during ankle inversion, one side of the body member 11 will compress and an opposite side will tend to extend. The stiffening unit 24 as secured to the body member 11-in conjunction with the stabilizing straps 57, 58-will resist and minimize the compression affecting one side of the body member. As a further advantage, the stiffening unit 24 does not obstruct the forward and rearward movement of upper portions 21A, 21B of the first and second side sections 14, 15 with respect to the bottom section 17. In other words, the stiffening unit 24 minimizes inversion and eversion of ankle without obstructing dorsiflexion and flexion.

One embodiment of the invention as illustrated in FIGS. 4 and 6 provides a two-piece stiffening unit 24. Specifically, the stiffening unit 24 may be formed from a base 27 and a cuff 28 that are pivotably connected to one another to define two pivot points 25, 26. The base 27 includes a first upright member 29 and a second upright member 30. The first and second upright members 29, 30 each have free ends and define substantially parallel planes. As depicted in FIGS. 1 and 3, each upright member 29, 30 extends upwardly from the base 27 along portions of the first and second side sections 14, 15 of the body member 11. Specifically, the first upright member 29 extends upwardly from an edge of the base 27. Likewise, the second upright member 30 extends upwardly from an edge of the base 27 substantially opposite the edge from which the first upright member 29 extends.

As illustrated in FIG. 6, the cuff 28 provides a first leg 35 and a second leg 36. The first and second legs 35, 36 each extend downwardly along a portion of the first and second side sections 14, 15 of the body member 11, respectively. More specifically, the first leg 35 extends downwardly from an edge of the cuff 28. The second leg 36 likewise extends downwardly from an edge of the cuff 28 substantially opposite the edge from which the first leg 35 extends. The first and second legs 35, 36 each have free ends and define substantially parallel planes. The free ends of the first and second upright members 29, 30 are pivotably connected to the free ends of the first and second legs 35, 36, respectively, to thereby define the pivot points 25, 26.

The cuff 28 extends about upper portions of the body member. In one embodiment, the cuff 28 extends substantially coextensive with upper portions 21A, 21B of the body member 11 and the rear section 16. For example, in one embodiment depicted in FIGS. 3 and 4, the cuff 28 extends coextensive with upper portions 21A, 21B of the first and second side sections 14, 15 and the rear section 16. As depicted in FIGS. 2 and 3, the cuff 28 extends circumferentially about portions of an upper ankle when the apparatus 10 is secured to an ankle. It will be understood that the invention does not require that the cuff 28 extend circumferentially about portions of an upper ankle or coextensive with upper portions 21A, 21B of the first and second side sections 14, 15 and the rear section 16.

Referring to FIGS. 1 and 2, the ankle stabilizing apparatus 10 further provides first and second stiffening unit connectors 37, 38 for pivotably connecting the free ends of the first and second upright members 29, 30 to the free ends of the first and second legs 35, 36, respectively. As illustrated in FIGS. 6 and 7, the free ends of the first and second upright members 29, 30 and the free ends of the first and second legs 35, 36 each define at least one opening 39. As configured, the first and second upright member openings 39 are coaxially aligned with the first and second leg openings 39 such that the openings are capable of receiving the first and second connectors 37, 38, respectively (see FIG. 6).

In one embodiment depicted in FIG. 7, the first and second stiffening unit connectors 37, 38 include a rivet 40 and a rivet backing 41 that secure free ends of the first and second upright members 29, 30 to free ends of the first and second legs 35, 36. In particular, the connectors 37, 38 secure the free ends of the first and second upright members 29, 30 and the free ends of the first and second legs 35, 36 between the rivet 40 and the rivet backing 41. It will be understood by those skilled in the art that the rivet 40 and rivet backing 41 may be formed from any number of materials sufficient to secure free ends of the first and second upright members 29, 30 to free ends of the first and second legs 35, 36 (e.g., plastic, stainless steel, etc.)

As illustrated in FIGS. 3, the invention further provides a cuff cover panel 42, a first and second stiffening unit cover strap 43, 44, and a first and second stiffening unit cover panel 45, 46. The cuff cover panel 42 secures selected portions of the stiffening unit 24, and specifically the cuff 28, to the body member 11. The cuff cover panel 42 is secured to the exterior surface 13 of upper portions 21A, 21B of the body member 11. In one embodiment, the cuff cover panel 42 is secured to exterior surfaces 13 of the first side section 14, the second side section 15, and the rear section 16 of the body member 11. It will be understood, however, that the cuff cover panel 42 may be secured only, for example, to one of the side sections 14, 15 or only to the rear section 16. The cuff cover panel 42 may also be secured to any combination of the side sections 14, 15 and rear section 16 so long as the cover panel 42 provides sufficient support to secure the cuff 28 to the body member 11. It will also be understood that in an alternative embodiment of the invention, the stiffening unit cover straps 43, 44 and the stiffening unit cover panels 45, 46 may be replaced with a single continuous stiffening unit cover strap that extends substantially the height of the body member to secure the first and second legs 35, 36 and the first and second upright members 29, 30 to the body member (see FIG. 8).

Still referring to FIG. 3, the cuff cover panel 42 extends substantially coextensive with upper portions 21A, 21B of first and second side sections 14, 15 of the body member 11, and more specifically, coextensive with the cuff 28. As depicted in FIGS. 3 and 5, portions of the stiffening unit 24, and specifically, the cuff 28 and first and second legs 35, 36 of the cuff, are positioned between the exterior surface 13 of the body member 11 and the cuff cover panel 42.

The invention further provides, in one embodiment, first and second stiffening unit cover straps 43, 44 for positioning selected portions of the stiffening unit 24 substantially adjacent the body member 11 as shown in FIGS. 3 and 5. More specifically, the first and second stiffening unit cover straps 43, 44 position the first and second legs 35, 36, and the first and second upright members 29, 30, substantially adjacent to the body member 11. The stiffening unit cover straps 43, 44 are secured to exterior surfaces 13 of the first and second side sections 14, 15 of the body member 11 with, for example, stitching. In one embodiment, selected edges of the first and second cover straps 43, 44 are secured to the first and second side sections 14, 15 of the body member 11, respectively, and to substantially opposing sides of the cuff 28 (see FIGS. 1 and 3). More specifically, selected edges of the first and second cover straps 43, 44 are secured to the first and second side sections 14, 15 of the body member 11, respectively, and to substantially opposing sides of the cuff cover panel 42.

The first and second stiffening unit cover straps 43, 44 extend substantially adjacent to a portion of the cuff 28, a portion of the first and second upright members 29, 30, or a portion of the first and second legs 35, 36. Stated differently, the first and second stiffening unit cover straps 43, 44 extend from an upper portion 21A, 21B of the first or second side sections 14, 15 to a lower portion 22A, 22B of the first or second side sections. As configured, portions of the stiffening unit 24, and specifically the cuff 28, first and second legs 35, 36, and first and second upright members 29, 30, are positioned between the exterior surface 13 of the body member 11 and the stiffening unit cover straps 43, 44 (see FIG. 5).

Referring to FIGS. 1, 3, and 5, the stiffening unit cover panels 45, 46 position selected portions of the stiffening unit 24, and specifically, the first and second upright members 29, 30, substantially adjacent to the body member 11. The stiffening unit cover panels 45, 46 are secured to exterior surfaces 13 of the first and second side sections 14, 15 by, for example, stitching. In one embodiment, selected edges of the first and second cover panels 45, 46 are secured to the first and second side sections 14, 15 of the body member 11, respectively. As illustrated in FIGS. 1 and 5, the cover panel 45, 46 is positioned substantially adjacent to the stiffening unit cover straps 43, 44. As configured, portions of the stiffening unit 24, and specifically the first and second upright members 29, 30, are positioned between the exterior surface 13 of the body member 11 and the stiffening unit cover panels 45, 46 as illustrated in FIG. 5.

With reference to FIG. 3, lower ends of the first and second cover straps 43, 44 are releasably secured to the first and second side sections 14, 15 of the body member 11 and specifically to the first and second cover panels 45, 46. Accordingly, the first and second cover straps 43, 44 permit access to the free ends of the first and second upright members 29, 30 and to free ends of the first and second legs 35, 36, respectively, as described below.

Still referring to FIG. 3, a first and second pair of corresponding fasteners 50A, 50B, 51A, 51B are provided to releasably secure portions of the first and second stiffening unit cover straps 43, 44 to portions of the first and second stiffening unit cover panels 45, 46. The first and second pairs of corresponding fasteners 50A, 50B, 51A, 51B are secured to an interior surface of the lower portion (i.e., free lower ends) of the first and second stiffening unit cover straps 43, 44 and to an exterior surface of the stiffening unit cover panels 45, 46, respectively. Advantageously, the pair of corresponding fasteners permits access to the pivot points 25, 26 of the stiffening unit 24. In particular, the fasteners permit access to the rivet 40 and rivet backings 41 that pivotably secure the free ends of the first and second upright members 29, 30 to the free ends of the first and second legs 35, 36. Accordingly, an individual can easily replace damaged rivets 40 or rivet backings 41 without disassembling the ankle brace.

In one embodiment, the stiffening unit 24 is secured to the body member 11 by stitching at the bottom section 17 and along upper edge portions 21A, 21B of the first and second side sections 14, 15 of the body member. In other words, the base 27 is secured to the body member 11 at the bottom section 17, and the cuff 28 is secured to the body member at the upper portions 21A, 21B of the first and second side sections 14, 15 (see FIGS. 1 and 3).

As depicted in FIGS. 3 and 5, the invention also provides padding 52 secured to the exterior surface 13 of the body member 11 and positioned substantially adjacent to the pivot points 25, 26 for minimizing contact between the stiffening unit 24 and an ankle. In one embodiment, the padding 52 is secured to exterior surfaces 13 of the first and second side sections 14, 15 of the body member 11 substantially adjacent to the free ends of the first and second upright members 29, 30 and the free ends of the first and second legs 35, 36. As positioned, the padding 52 is located between the body member 11 and the free ends of the first and second upright members 29, 30 and free ends of the first and second legs 35, 36 (see FIG. 5).

Padding 52 is also provided on interior portions of the stiffening unit 24 for minimizing contact between the stiffening unit and an ankle (see FIG. 5). In one embodiment, padding 52 is secured to interior portions of the cuff 28 and first and second legs 35, 36.

The padding 52 may be a sheet or sheets of foam material. It will be understood that the padding 52 may be continuous or patterned. Those skilled in the art will also appreciate that the sheet of foam material forming the padding 52 may be any number of shapes (i.e., L-shaped, C-shaped, rectangular, circular, trapezoidal, etc.).

With reference to FIGS. 1, 2, and 3, the ankle stabilizing apparatus 10 further provides a body member connector 53 for securing free front edges of the first and second side sections 14, 15 to one another to thereby secure the body member 11 and stiffening unit 24 to an ankle. The body member connector 53 facilitates the drawing of the front edges of the first and second side sections 14, 15 towards one another to secure the apparatus 10 about the ankle and foot. In one embodiment, the body member connector 53 may comprise a plurality of eyelets 54 defined by and extending along front edges of the first and second side sections 14, 15 of the body member 11, a plurality of eyelets defined by and extending along front edges of the stiffening unit 24, and at least one lace 55 threaded through the respective eyelets. As constructed, the eyelets 54 of the stiffening unit 24 correspond to the eyelets of the first and second side sections 14, 15 to permit the threading of the lace 55 therethrough.

It will be understood, however, that the body member connector 53 may include any number of devices capable of drawing the front edges of the first and second side sections 14, 15 together. For example, the connector 53 may include at least one strap having one end fixed to at least one front edge of the first or second side sections 14, 15 and an opposite free end. The alternative embodiment of the connector 53 may include at least one corresponding pair of fasteners, wherein one fastener is secured to a free end of the strap and a second fastener is secured to a corresponding front edge of the first or second side sections 14, 15 opposite the edge to which the strap is secured. In yet another embodiment of the connector 53, a plurality of straps having a plurality of fasteners may be provided, wherein the straps are secured to a front edge of one of the first or second side sections 14, 15. Corresponding pairs of fasteners are disposed on a free end of the strap and a corresponding edge of the first or second side sections 14, 15 opposite the edge to which the straps are secured. Alternatively, the straps and fasteners may be disposed in alternating fashion the length of the free edges of the first and second side sections 14, 15.

As illustrated in FIGS. 1-3, a binding strip 56 may be sewn along the front edges of first and second side sections 14, 15, along edges of the first and second side sections defining the heel opening 23, along the top edges of the first and second side sections, and along front edges of the bottom section 17 of the body member 11 to provide non-raveling edges and a finished appearance to the apparatus 10.

As illustrated in FIGS. 2 and 3, the apparatus 10 also desirably includes first and second substantially inelastic stabilizing straps 57, 58 which are attached to the body member 11. Each stabilizing strap 57, 58 includes a first end 57A, 58A secured to at least a portion of the body member 11, and an opposite second end or free end 57B, 58B. In one embodiment, the first ends 57A, 58A of the stabilizing straps 57, 58 are secured to the rear section 16 of the body member 11 adjacent to the ankle. The stabilizing straps 57, 58 may be secured to the body member 11 in a releasable manner (e.g., by hook and loop fasteners) or permanent manner (e.g., by sewing). In the illustrated embodiment, the stabilizing straps 57, 58 are secured to the rear section 16 by sewing along a seam line. The stabilizing straps 57, 58 can be formed individually or (as in the form of the invention shown in FIGS. 1 and 3) from a single piece of material which is seamed along a central portion thereof to the body member 11 to thereby form two stabilizing straps. As referenced above, the first strap 57 has a fixed first end 57A and a free opposite end 57B, and the second strap 58 has a fixed first end 58A and an opposite free end 58B.

The first stabilizing strap 57 extends laterally from the rear section 16 of the body member 11 toward the first side section 14, while the second stabilizing strap 58 extends laterally from the rear section 16 of the body member toward the second side section 15. The straps 57, 58 are preferably formed from a strapping-type material such as a ballistic nylon fabric. In one embodiment of the invention, the stabilizing straps 57, 58 are attached at or near the rear section 16 of the body member 11 at a sufficient height to minimize inversion and eversion of the ankle, yet permit flexion and dorsiflexion.

For the purpose of securing the stabilizing straps 57, 58 about the foot in the manner described below, there is provided a first and second pair of corresponding fasteners 59, 60 associated with the first and second stabilizing straps 57, 58. The first pair of corresponding fasteners 59 includes a first fastener 59A attached to the exterior surface 13 of the first side section 14, and a second fastener 59B attached to the free end 57B of the first stabilizing strap 57. Specifically, in one embodiment, the first fastener 59A is secured to the first stiffening unit cover strap 43 as illustrated in FIGS. 1 and 3. The second pair of corresponding fasteners 60 includes a first fastener 60A attached to the exterior surface 13 of the second side section 15, and a second fastener 60B attached to the free end 58B of the second stabilizing strap 58. Specifically, in one embodiment, the first fastener 60A is secured to the second stiffening unit cover strap 44. The corresponding fastener pairs 59, 60 may be in the form of hook and loop fasteners of the type sold under the trademark VELCRO®.

The first fasteners 59A, 60A of the first and second pair of corresponding fasteners 59, 60 are preferably elongate and extend vertically from an upper portion of the body member 11 downwardly toward the bottom section 17 of the body member (i.e., along the stiffening unit cover straps 43, 44).

The second fasteners 59B, 60B of the first and second pair of corresponding fasteners 59, 60 are likewise preferably elongate to thereby ensure secure attachment points.

As depicted in FIGS. 1, 2, and 3, a tongue 61 is secured between the opposing free front edges of the body member 11. The tongue 61 is preferably fixed to a front edge of at least one of the first and second side sections 14, 15 and may be composed of a padded fabric. The tongue 61 assists to secure the body member 11 to the foot of the individual, and provides padding between the body member connector 53 and the individual's foot.

Referring to FIG. 3, one embodiment of the invention may also provide a protective backing panel 62 that extends from the upper edge of the body member 11, along the length of the rear section 16 of the body member, and to an upper edge of the body member opening 23. The protective backing 62 may be secured (e.g., stitched) at one end to the upper edge of the body member 11 and secured at an opposite end to the upper edges of the body member opening 23. As illustrated in FIG. 5, the protective backing 62 may extend into and across a portion of the body member opening 23 to thereby provide a cushion for the upper heel of the individual. One embodiment of the protective backing 62 is substantially rectangular in shape, but may take the form of any number of shapes sufficient to cover the rear section 16 of the body member 11 (e.g., trapezoidal or polygonal).

The invention further provides first and second binding straps 63, 64 configured to loop about the ankle of the wearer so as to overlie portions of the stabilizing straps 57, 58, lace 55, and eyelets 54. Preferably, the binding straps 63, 64 are secured to the rear section 16 of the body member 11, and include at least one free end as illustrated in FIG. 3. In this fashion, the binding straps 63, 64 may be wrapped circumferentially about the individual's ankle to secure the body member 11 and stiffening unit 24 more securely to the individual's foot. Though specifically illustrated in FIG. 2 as being in the form of a single binding strap 63 secured to the rear section 16 of the body member 11 to thereby provide two free ends, it will be appreciated that a single strap could be secured at one end and have a single free end which wraps around the individual's ankle. Alternatively, a plurality of straps may form the binding strap.

The binding straps 63, 64 desirably extend laterally from the rear section 16 of the body member 11 to overlie at least a portion of the stabilizing straps 57, 58. The free ends of the binding straps 63, 64 are secured so that the binding straps encircle the individual's ankle by way of a pair of corresponding fasteners 65A, 65B. The pair of corresponding fasteners 65A, 65B is preferably secured to free ends of the binding strap such that the free ends engage one another when wrapped around the ankle and extended against one another in overlying fashion. The fasteners 65A, 65B are desirably of the hook and loop fastener variety, though other types of fasteners may be used. In one embodiment of the invention, the binding straps 63, 64 are made from an elastic fabric material.

In operation, the body member 11 is first secured on the individual's foot. The first stabilizing strap 57 is then brought across the first side section 14 of the body member 11, over the top of the individual's foot, downwardly across the inside of the foot, and under the foot. The first stabilizing strap 57 is then brought upwardly so that the fastener 59B on the free end 57B thereof can be attached to its corresponding fastener 59A on the exterior surface 13 of the first stiffening member cover strap 43.

The second stabilizing strap 58 is then wrapped around the individual's foot by bringing it across the second side section 15, over top of the individual's foot, downwardly across the outside of the foot, under the foot, and then upwardly so that the fastener 60B on the free end 58B thereof can be secured to the fastener 60A located on the second stiffening member cover strap 44.

As illustrated in FIGS. 1 and 2, the body member 11 is adapted to be placed on the appropriate foot of the wearer, preferably on the skin or over top of an athletic sock. Once the body member 11 is secured to the foot, the lace 55 is drawn tight and secured (e.g., by tying the lace into a knot). The stabilizing straps are then wrapped around the upper ankle for secure fitment.

In the drawings and specification, there have been disclosed typical embodiments on the invention and, although specific terms have been employed, they have been used in a generic and descriptive sense only and not for purposes of limitation, the scope of the invention being set forth in the following claims.

That which is claimed is:

1. An apparatus for stabilizing movement of an ankle, said apparatus comprising:
   a flexible body member for receiving a foot, said body member defining a first side section, a second side section connected to at least one edge of said first side section, a rear section defined by rear portions of said first and second side sections, a bottom section defined by lower portions of said first and second side sections, and at least one opening for receiving a heel, said body member having an interior surface and an exterior surface;
   a stiffening unit secured to selected portions of said body member, said stiffening unit having at least one pivot point positioned between an upper end and a lower end of said stiffening unit; and
   a body member connector for securing free front edges of said first and second side sections to one another to thereby secure said body member to an ankle, said connector comprising:
      a plurality of eyelets extending along free front edges of said first and second side sections of said body member;
      a plurality of eyelets extending along free front edges of said stiffening unit, said stiffening unit eyelets corresponding to said first and second side section eyelets; and
      and at least one lace threaded through said respective eyelets;
   wherein said stiffening unit minimizes lateral and vertical movement of upper portions of said body member with respect to said bottom section, without obstructing forward and rearward movement of upper portions of said body member with respect to said bottom section.

2. An ankle stabilizing apparatus according to claim 1, wherein said body member is formed from inelastic material.

3. An ankle stabilizing apparatus according to claim 1, wherein said body member consists essentially of a one-piece body member.

4. An ankle stabilizing apparatus according to claim 1, wherein said body member consists essentially of a multi-piece body member.

5. An ankle stabilizing apparatus according to claim 1, wherein said second side section of said body member is connected to said first side section of said body member along said bottom section of said body member.

6. An ankle stabilizing apparatus according to claim 1, wherein said second side section of said body member is connected to said first side section of said body member along said rear section of said body member.

7. An ankle stabilizing apparatus according to claim 1, wherein said stiffening unit is formed from polymeric material.

8. An ankle stabilizing apparatus according to claim 1, wherein said stiffening unit is a two-piece stiffening unit.

9. An ankle stabilizing apparatus according to claim 1, wherein said stiffening unit is secured to said body member at said bottom section of said body member.

10. An ankle stabilizing apparatus according to claim 1, wherein said stiffening unit is secured to said body member along upper edge portions of said first and second side sections of said body member.

11. An ankle stabilizing apparatus according to claim 1, said stiffening unit comprising:
    a base having a first upright member and a second upright member, said first upright member and said second upright member having free ends and defining substantially parallel planes; and
    a cuff having a first leg and a second leg, said first leg and said second leg having free ends and defining substantially parallel planes;
    wherein said free ends of said first and second upright members are pivotably connected to said free ends of said first and second legs, respectively, to form said at least one pivot point.

12. An ankle stabilizing apparatus according to claim 11, further comprising first and second stiffening unit connectors for pivotably connecting said free ends of said first and second upright members to said free ends of said first and second legs, respectively.

13. An ankle stabilizing apparatus according to claim 11, wherein said cuff extends substantially coextensive with upper portions of said body member.

14. An ankle stabilizing apparatus according to claim 11, wherein said cuff extends about portions of an upper ankle when said apparatus is secured to an ankle.

15. An ankle stabilizing apparatus according to claim 1, said body member further comprising:
    at least one cuff cover panel for securing selected portions of said stiffening unit to said body member, said cuff cover panel secured to upper portions of said body member.

16. An ankle stabilizing apparatus according to claim 15, wherein said cuff cover panel extends substantially coextensive with upper portions of said first and second side sections of said body member.

17. An ankle stabilizing apparatus according to claim 15, wherein portions of said stiffening unit are positioned between said exterior surface of said body member and said cuff cover panel.

18. An ankle stabilizing apparatus according to claim 1, said body member further comprising:
    at least one stiffening unit cover strap for positioning selected portions of said stiffening unit substantially adjacent to said body member, said stiffening unit cover strap secured to said first and second side sections of said body member.

19. An ankle stabilizing apparatus according to claim 18, said body member further comprising:
    at least one stiffening unit cover panel for positioning selected portions of said stiffening unit substantially adjacent to said body member, said stiffening unit cover panel secured to said first and second side sections substantially adjacent to said stiffening unit cover strap.

20. An ankle stabilizing apparatus according to claim 19, wherein portions of said stiffening unit are positioned between said exterior surface of said body member and said stiffening unit cover panel.

21. An ankle stabilizing apparatus according to claim 19, further comprising:
    at least one pair of corresponding fasteners secured to an interior surface of said stiffening unit cover strap and to an exterior surface of said stiffening unit cover panel, respectively, such that a portion of said stiffening unit cover strap is releasably secured to a portion of said stiffening unit cover panel, said pair of corresponding fasteners permitting access to said at least one pivot point of said stiffening unit.

22. An ankle stabilizing apparatus according to claim 18, wherein said stiffening unit cover strap extends from an upper portion of said first or second side section to a lower portion of said first or second side section.

23. An ankle stabilizing apparatus according to claim 18, wherein portions of said stiffening unit are positioned between said exterior surface of said body member and said stiffening unit cover strap.

24. An ankle stabilizing apparatus according to claim 1, further comprising:
    padding secured to said exterior surface of said body member substantially adjacent to said at least one pivot point for minimizing contact between said stiffening unit and an ankle.

25. An ankle stabilizing apparatus according to claim 1, further comprising:
    padding secured to interior portions of said stiffening unit for minimizing contact between said stiffening unit and an ankle.

26. An ankle stabilizing apparatus according to claim 1, further comprising:
    first and second stabilizing straps for securing said body member and said stiffening unit to an ankle in an overlying fashion, said straps each having a first end connected to at least a portion of said body member and a free end;
    a first pair of corresponding fasteners secured to an exterior surface of said first side section of said body member and to a free end of said first stabilizing strap, respectively; and
    a second pair of corresponding fasteners secured to an exterior surface of said second side section of said body member and to a free end of said second stabilizing strap, respectively.

27. An ankle stabilizing apparatus according to claim 1, further comprising a tongue fixed to a front edge of at least one of said first and second side sections.

28. An ankle stabilizing apparatus according to claim 1, further comprising:
    at least one binding strap secured to an upper portion of said body member, said binding strap releasably secured at one end to said body member for securing said binding strap about said body member.

29. An ankle stabilizing apparatus according to claim 1, further comprising at least one protective backing panel secured to said interior surface of said body member, said backing panel extending substantially vertical along at least a portion of said rear section of said body member.

30. An apparatus for stabilizing movement of an ankle, said apparatus comprising:
    a flexible body member for receiving a foot, said body member defining a first side section, a second side section connected to at least one edge of said first side section, a rear section defined by rear portions of said first and second side sections, a bottom section defined by lower portions of said first and second side sections, and at least one opening for receiving a heel, said body member having an interior surface and an exterior surface;

a semi-rigid base secured to said bottom section of said body member, said base having a first upright member and a second upright member that each extend along at least a portion of said first and second side sections of said body member, respectively, said first and second upright members defining free ends;

a semi-rigid cuff secured to upper portions of said body member, said cuff having a first leg and a second leg that each extend along at least a portion of said first and second side sections, respectively, said first and second legs defining free ends; and first and second stiffening unit cover straps for positioning said first and second legs, and said first and second upright members, substantially adjacent to said body member, lower ends of said first and second cover straps releasably secured to said first and second side sections of said body member, respectively, such that said first and second cover straps permit access to said free ends of said first and second upright members and to said free ends of said first and second legs, respectively, selected edges of said first and second cover straps secured to said first and second side sections of said body member, respectively, and to substantially opposing sides of said cuff;

wherein said free ends of said first and second upright members are pivotably connected to said free ends of said first and second legs, respectively, to thereby minimize inversion and eversion of an ankle supported by said apparatus without obstructing flexion and dorsiflexion of the ankle.

31. An ankle stabilizing apparatus according to claim 30, wherein:
said first upright member extends upwardly from an edge of said base; and
said second upright member extends upwardly from an edge of said base substantially opposite the edge from which said first upright member extends.

32. An ankle stabilizing apparatus according to claim 30, wherein:
said first leg extends downwardly from an edge of said cuff; and
said second leg extends downwardly from an edge of said cuff substantially opposite the edge from which said first leg extends.

33. An ankle stabilizing apparatus according to claim 30, wherein said body member is formed from inelastic material.

34. An ankle stabilizing apparatus according to claim 30, wherein said body member consists essentially of a one-piece body member.

35. An ankle stabilizing apparatus according to claim 30, wherein said body member consists essentially of a multi-piece body member.

36. An ankle stabilizing apparatus according to claim 30, wherein said first side section of said body member is connected to said second side section of said body member along said bottom section of said body member.

37. An ankle stabilizing apparatus according to claim 30, wherein said first side section of said body member is connected to said second side section of said body member along said rear section of said body member.

38. An ankle stabilizing apparatus according to claim 30, wherein said base is secured to said body member at said bottom section.

39. An ankle stabilizing apparatus according to claim 30, said body member further comprising:
at least one cuff cover panel for securing said cuff to said body member, said cuff cover panel secured to at least a portion of said first side section, or at least a portion of said second side section, or at least a portion of said rear section of said body member.

40. An ankle stabilizing apparatus according to claim 39, wherein said cuff cover panel extends substantially coextensive with said cuff.

41. An ankle stabilizing apparatus according to claim 30, wherein said first and second stiffening unit cover straps extend substantially adjacent to at least a portion of said cuff, at least a portion of said first and second upright members, and at least a portion of said first and second legs.

42. An ankle stabilizing apparatus according to claim 30, said body member further comprising:
first and second stiffening unit cover panels for positioning said first and second upright members substantially adjacent to said body member;
wherein selected edges of said first and second cover panels are secured to said first and second side sections of said body member, respectively.

43. An ankle stabilizing apparatus according to claim 30, further comprising:
padding secured to exterior surfaces of said first and second side sections of said body member substantially adjacent to said free ends of said first and second upright members and said free ends of said first and second legs, said padding positioned between said body member and said free ends.

44. An ankle stabilizing apparatus according to claim 30, further comprising:
padding secured to interior portions of said cuff for minimizing contact between said cuff and an ankle.

45. An ankle stabilizing apparatus according to claim 30, further comprising a body member connector for securing front edges of said first and second side sections of said body member to one another to thereby secure said body member and said stiffening unit to an ankle.

46. An ankle stabilizing apparatus according to claim 30, further comprising:
first and second stabilizing straps for securing said body member to an ankle and foot in an overlying fashion, said straps each having a first end connected to at least a portion of said body member and a free end;
a first pair of corresponding fasteners secured to an exterior surface of said first side section of said body member and to a free end of said first stabilizing strap, respectively; and
a second pair of corresponding fasteners secured to an exterior surface of said second side section of said body member and to a free end of said second stabilizing strap, respectively.

47. An ankle stabilizing apparatus according to claim 30, further comprising:
at least one binding strap secured to a portion of said body member; and
a pair of corresponding fasteners secured to free ends of said binding strap for securing said binding strap about said body member.

48. An apparatus for stabilizing movement of an ankle, said apparatus comprising:

a flexible body member for receiving a foot, said body member defining a first side section, a second side section connected to at least one edge of said first side section, a rear section defined by rear portions of said first and second side sections, a bottom section defined by lower portions of said first and second side sections, and at least one opening for receiving a heel, said body member having an interior surface and an exterior surface;

a semi-rigid base secured to said bottom section of said body member, said base having a first upright member and a second upright member each having free ends and each extending upwardly from edges of said base and along at least a portion of said first and second side sections, respectively;

a semi-rigid cuff secured to upper portions of said body member, said cuff having a first leg and a second leg each having free ends and each extending downwardly from edges of said cuff and along at least a portion of said first and second side sections, respectively;

a cuff cover panel for securing said cuff to said body member, said cuff cover panel secured to said exterior surface said body member, said cuff cover panel extending substantially coextensive with said cuff;

first and second cover straps for positioning said first and second legs and said first and second upright members substantially adjacent to said body member, said first and second cover straps secured to said first and second side sections of said body member, respectively, and to substantially opposing sides of said cuff; and first and second cover panels for positioning said first and second upright members substantially adjacent to said body member, said first and second cover panels secured to said first and second side sections of said body member, respectively;

wherein said free ends of said first and second upright members are pivotably connected to said free ends of said first and second legs, respectively, to form at least one pivot point;

wherein said base and said cuff minimize lateral and vertical movement of upper portions of said body member with respect to said bottom section, without obstructing forward and rearward movement of upper portions of said body member with respect to said bottom section.

* * * * *